United States Patent [19]

Doleschel et al.

[11] Patent Number: 4,803,073

[45] Date of Patent: Feb. 7, 1989

[54] PROCESS FOR THE PASTEURIZATION OF PLASMA PROTEINS AND PLASMA PROTEIN FRACTIONS

[75] Inventors: Walter Doleschel; Walter N. Doleschel, both of Vienna; Helmut Kaltschmid, Bad Vöslau, all of Austria

[73] Assignee: Schwab & Co Ges.m.b.H., Vienna, Austria

[21] Appl. No.: 23,185

[22] Filed: Mar. 9, 1987

[30] Foreign Application Priority Data

Mar. 18, 1986 [AT] Austria ................................... 719/86

[51] Int. Cl.[4] ..................... A61K 35/16; A61K 37/02; C12N 7/06
[52] U.S. Cl. ...................................... 424/101; 424/95; 530/380; 530/381; 530/382; 530/383; 530/384; 530/385; 530/386; 530/387; 530/388; 530/389; 530/427; 514/802; 514/2; 514/21; 435/236; 435/238
[58] Field of Search ............... 514/802, 546, 549, 552; 435/236, 238; 252/70, 71, 73, 79; 424/101, 95; 530/380–389, 427; 422/46

[56] References Cited

U.S. PATENT DOCUMENTS

| | | | |
|---|---|---|---|
| 4,481,189 | 11/1984 | Prince | 424/101 |
| 4,490,361 | 12/1984 | Heldebrant | 424/101 |
| 4,613,501 | 9/1986 | Horowitz | 435/238 |
| 4,640,834 | 2/1987 | Eibl et al. | 435/238 |

FOREIGN PATENT DOCUMENTS

| | | |
|---|---|---|
| 110407 | 6/1984 | European Pat. Off. . |
| 112563 | 7/1984 | European Pat. Off. . |
| 8304371 | 12/1983 | PCT Int'l Appl. . |

*Primary Examiner*—Johnnie R. Brown
*Assistant Examiner*—Jacqueline M. Stone
*Attorney, Agent, or Firm*—Mark Dryer

[57] ABSTRACT

The invention relates to a process for the pasteurization of plasma proteins and plasma protein fractions without essentially impairing their biological activity, by subjecting a suspension of the plasma proteins or plasma protein fractions in glycerol esters of saturated or singly or multiply unsaturated fatty acids having 4–22 carbon atoms, or mixtures of these esters, as the inert heat-transfer agent, with a maximum water content of the suspension of 1% by weight, to a heat treatment at temperatures of 50° to 120° C.

8 Claims, No Drawings

PROCESS FOR THE PASTEURIZATION OF PLASMA PROTEINS AND PLASMA PROTEIN FRACTIONS

DESCRIPTION

The invention relates to a new process for the pasteurization of plasma proteins and plasma protein fractions without essentially impairing their biological activity.

The administration of plasma proteins or plasma protein fractions from human plasma to patients is an indispensable method of treatment in many cases of illness but is associated with the risk of transmitting viral infectious diseases. Although this risk can be diminished by careful selection of donors and thorough testing, nevertheless the risk of infection cannot be overlooked when there is continual administration of plasma proteins, for example to hemophilic patients.

Thus there have been attempts in progress for some time to eliminate the risk of infection by virus inactivation, which can be achieved in particular by heat treatment of the plasma proteins or individual fractions thereof. This is impeded by the fact that whereas albumin and heat-resistant alpha- and beta-globulins can, under certain conditions, be pasteurized in aqueous solution, other selected plasma protein fractions, such as immunoglobulins or clotting factors, and among them in particular, concentrates of antihemophilic factors, lose their biological activity either entirely or to a very large extent.

There have already been several proposals that, to avoid these difficulties, plasma proteins be stabilized against the action of heat in aqueous solution by various additives such as amino acids, saccharides, sugar alcohols, Ca ions, potassium or ammonium citrate or salts of carboxylic acids and hydroxy carboxylic acids (compare, inter alia, U.S. Pat. Nos. 4,297,344, 4,440,679, 4,327,086 and 4,446,134, German Offenlegungsschriften Nos. 3,237,512 and 3 330 770 and PCT Application WO No. 83/04027), but in this method it is necessary to accept serious losses of biological activity.

A multistage process for the removal of hepatitis B viruses and non-A, non-B hepatitis viruses in biological material is described in European Pat. No. A-110,407. This process includes, in one of the steps, a heat treatment of the biological material, in which, according to the statements in the citation, the loss of activity at pasteurization temperatures of 55°–70° C. is found to be only 10–25%. However, this dry-heating process has, in any event, the disadvantage that the transfer of heat is far from uniform, especially with relatively large amounts of biological material, which means that, on the one hand, the biological material may be damaged due to local overheating and, on the other hand, the virus inactivation may be deficient in places where the transfer of heat is low.

Processes for eliminating infectious viruses and pyrogenic substances exclusively having a lipid structure are disclosed in European Pat. No. A-112 563 and PCT/WO No. 83/04371, in which the lipid envelope of these pathogens is destroyed by extractive treatment with lipophilic solvents, preferably with chlorinated hydrocarbons, at room temperature, which results in their inactivation. However, European Pat. No. A-112 563 expressly advises against heat treatment to avoid damage to the plasma proteins, so that only pathogens with a lipid structure can be eliminated, whereas other types of pathogens are not amenabe to inactivation by this method. Finally, there is a proposal in U.S. Pat. No. 4,490,361 to subject suspensions of dried plasma proteins in organic solvents to heat treatment for virus inactivation. The solvents mentioned as suitable in the citation are liquid alkanes such as hexane or heptane, ketones such as acetone or diethyl ketone or perfluorinated compounds such as perfluorotripropylamine. Although the transfer of heat in suspensions is sure to be satisfactory and uniform, the process according to U.S. Pat. No. 4,490,361 is not entirely satisfactory since it is still necessary to accept considerable losses of activity. Thus, after a lyophilized AHF preparation has been heated in acetone, hexane or perfluorotripropylamine for ten hours, at a temperature in the region of 60° C., which is, however, at the lower limit for effective pasteurization, retains only between 59.7 and 70.7% of its original biological activity, for example.

Thus, there continues to be a need for an improved pasteurization process for plasma proteins, the object being to ensure not only that transfer of heat is satisfactory and uniform and that there is reliable virus inactivation, but also that the biological activity is retained as far as possible. In addition, in terms of its elaboration the process should be economic and straightforward to carry out.

It has now been found, surprisingly, that glycerol esters of saturated and unsaturated fatty acids, as occur, for example, in biological oils, liquified fats and partially or completely hydrogenated oils, are an excellent pasteurization medium in which the heat treatment for virus inactivation of plasma proteins and plasma protein fractions can be carried out in a straightforward manner with substantial retention of the biological activity.

Accordingly, the invention relates to a process for the pasteurization of dried plasma proteins and plasma protein fractions by heat treatment of their suspensions in a liquid organic heat-transfer agent without essentially impairing their biological activity, the process comprising the heat treatment being carried out in symmetrical or mixed glycerol esters, which are liquid at the pasteurization temperature, of saturated or singly or multiply unsaturated fatty acids having 4–22 carbon atoms, or mixtures of these esters, as the inert heat-transfer agent, with the maximum water content of the suspension being 1% by weight and the temperature being 50°–120° C.

The glycerol esters which are used as heat-transfer agents for the process according to the invention and in which the plasma proteins and plasma protein fractions are suspended for the heat treatment can be synthetic in nature. However, the glycerol esters are preferably derived from natural sources, vegetable or animal, and, as such, are biological oils, liquified fats or semisynthetic products, such as partially or completely hydrogenated oils. The vegetable and animal fats and oils which are particularly suitable for the pasteurization essentially comprise mixed glycerol esters of higher fatty acids. Possible examples of these are glycerol esters of saturated fatty acids of the general formula $C_nH_{2n+1}COOH$, in which n denotes an integer from 4 to 22, of singly unsaturated fatty acids of the general formula $C_nH_{2n-1}COOH$, in which n denotes an integer from 16 to 22, or of multiply unsaturated fatty acids with a molecular formula from $C_{19}H_{32}O_2$ to $C_{22}H_{34}O_2$, the composition of the fatty acids with which the glycerol is esterified being unimportant. Fatty acids which frequently occur in these natural glycerol esters are palmitic acid ($C_{15}H_{31}COOH$), stearic acid ($C_{17}H_{35}COOH$) and oleic acid ($C_{17}H_{33}COOH$). In addition, natural glycerol esters are found also to contain lauric acid, butyric acid, the unsaturated palmitoleic acid, the highly unsaturated linoleic acid and, in lower concentration, also other fatty acids such as caproic acid, capric acid, caprylic acid, arachic acid, linolenic acid and the like.

Apart from synthetic and natural glycerol esters, also suitable for the pasteurization process are the semisynthetic products produced by what is called fat hardening (hydrogenation). These result from catalytic addition of hydrogen onto unsaturated fatty acids in the glycerol esters which occur in natural fats and oils, there being, for example, conversion of unsaturated oleic acid into saturated stearic acid, and of ricinoleic acid into hydroxystearic acid.

As a rule, the natural and semisynthetic fats and oils are not composed of symmetrical esters having the same fatty acid components but are composed of mixed esters of glycerol and fatty acids. Fresh fats and oils are always neutral fats in which all three OH groups of the glycerol are esterified with fatty acids.

Examples of glycerol esters of the abovementioned composition from vegetable sources are corn oil, sunflower oil, olive oil, wheatgerm oil, rape oil, soybean oil, thistle oil, kernel oils from other sources, and the like.

Suitable glycerol esters from animal sources are milk fats or tissue fats, for example the fats occurring in butter or butter fat, which are essentially composed of butyrodiolein, butyroplamitolein, oleodiplamitin, palmitodistearin, stereodipalmitin and tristearin, lard, which comprises pure pork fat with a water content of less than 0.3% and is mainly composed of mixed glycerol esters of oleic acid, palmitic acid and stearic acid, or beef tallow and the like.

Suitable semisynthetic products which are obtained by fat hardening and are envisaged as heat-transfer agents for the process according to the invention are edible fats or margarines of a variety of compositions and origins.

In most cases, the glycerol esters used as heat-transfer agents in the pasteurization can be employed, without further pretreatment, in the form of the commercially available fats and oils supplied by the foodstuffs industry. The additives which are customarily present in small amounts, such as mineral salts, vitamins and amino acids or emulsifiers, do not interfere in the process according to the invention. However, care must be taken that the water content in the suspension is not more than 1% by weight. A higher water content in the suspension of the plasma proteins and plasma protein fractions may result in extensive denaturation of the proteins and thus in a considerable loss of their biological activity. Thus, for example, the products obtained on the heat treatment of antihemophilic plasma (AHP) in a suspension of lard which contains 2% by weight of water have, after a pasteurization time of 21.5 hours at 60° C., a clotting activity which is now only 20% of the initial activity before the pasteurization.

It is advantageous for the water content in the suspension of the plasma proteins or their fractions which are to be pasteurized not to exceed 0.5% by weight. Fats and oils which, owing to their nature or manufacture, have a higher water content are expediently dried before use in order to reduce the water content, for example by centrifugation of the liquified fats or by treatment with anhydrous inorganic hygroscopic substances such as, for example, $Na_2SO_4$ or $CaCl_2$.

It has been found moreover that the addition of Ca salts to the suspension has in many cases a particularly favorable effect on the retention of the biological activity of the plasma proteins during the pasteurization. Particularly with certain clotting factors, such as, for example, factor VIII, factor IX and fibrinogen, which are active in conjunction with Ca ions, it has been found that addition of Ca salts results in virtually 100% stability of their clotting activity after the pasteurization. Hence, in a preferred embodiment of the process according to the invention, the heat treatment of the plasma proteins is carried out in the presence of Ca salts in the suspension in an amount of 10 to 50 mmol per liter.

The process according to the invention can be applied to plasma proteins or plasma protein fractions which have been isolated in a known manner from human blood plasma, for example, antithrombin III, factor VIII, fibrinogen, the proteins of the prothrombin complex, such as factors II, VII, IX and X, protein C, protein S, immunoglobulins, freeze-dried fresh plasma and the like. The preparation of these plasma proteins and the plasma protein fractions is known and has been described many times in the relevant literature.

The plasms proteins or plasma protein fractions are used for the pasteurization process according to the invention in dried form, as obtained, for example, by lyophilization, spray-drying or other non-damaging drying methods from the aqueous solutions of the plasma proteins which result from the fractionation. The latter are then converted into a finely divided form and suspended in the particular heat-transfer agent selected for the heat treatment. If the glycerol esters selected as heat-transfer agents are in the solid state of aggregation or in the form of viscous oils at room temperature, it is advisable to convert the heat-transfer agent, by warming, into a mobile state of aggregation before the addition of the plasma proteins to prepare the suspension. The plasma proteins are insoluble in the glycerol esters envisaged for the process according to the invention. The temperature and treatment time for the pasteurization according to the invention are based on the figures customary for the pasteurization of plasma fractions.

In general, it is possible to use temperatures of 50°–120° C. and pasteurization times from 2 hours up to several days, but other variants, such as, for example, shock-type heating for only a few seconds are also possible. The duration of the heat treatment depends on the selected temperature. The temperature range which has proved particularly favorable for non-damaging treatment of the plasma proteins and reliable virus inactivation is 60°–70° C. with a pasteurization time of 10 to 48 hours. As a rule, of course, the decrease of the biological activity increases with the duration of the treatment and at higher temperatures. However, in comparison with the processes of the prior art, surprisingly little damage results from the process according to the invention. Thus, for example, on pasteurization according to the invention of various production batches of factor VIII concentrates, these preparations retain 90–100% of the original AHF activity with a treatment time of 16 hours and a treatment temperature of 60° C.

The working up and purification of the plasma proteins and plasma protein fractions after the pasteurization according to the invention is complete are very straightforward. The heat-transfer agent which has been used can be removed by filtering off, optionally with suction, the plasma proteins, it bbeing expedient in many cases to remove the heat-transfer agent immediately after completion of the heat treatment before the latter has solidified or become viscous. However, it is also possible to remove the heat-transfer agent by treatment with organic solvents. Thus, for example, in cases in which the heat-transfer agent is to be completely removed before the subsequent processing of the plasma proteins or for the purpose of storage, it is advisable to wash the plasma proteins with an anhydrous volatile organic solvent in which the heat-transfer agent which is used is readily soluble, for example with n-hexane, petroleum ether, white spirit and the like. It is then possible and expedient to remove entirely the volatile washing agent in vacuo, where appropriate with gentle warming.

Apart from the surprisingly non-damaging treatment of the plasma proteins with the greatest possible retention of their biological activity, the pasteurization process according to the invention has the advantage that the heat-transfer agents which are used can be obtained from natural biological sources, and thus absolutely no toxicity problems arise. In addition, the process is straightforward to carry out and makes it possible to heat-inactivate pathogens under extremely economic conditions in heat-transfer agents which can be readily obtained at a reasonable cost.

The examples which follow illustrate the invention in detail:

EXAMPLE 1

1 g samples of freeze-dried preparation were taken from three production batches of factor VIII produced by known methods and one batch of freeze-dried fresh plasma (AHP), and each was mixed with 10 g of a commercially available dried sunflower oil at 60° C. (The oil had been dried with anhydrous $CaCl_2$ powder at 60° C. for 2 hours and been separated from the $CaCl_2$ by decantation before mixing with the protein fractions).

The protein-oil suspensions were pasteurized in an incubator at 60° C.+−0.2° C. for 16 hours. After the pasteurization was complete the still warm oil was removed by filtration with suction, and the preparation was then washed four times with n-hexane and dried, first in the air and then in vacuo.

The biological factor VIII activities were the following percentages of the initial value before the pasteurization:

Batch I 89.5%
Batch II 100.0%
Batch III 93.3%
AHP Batch 90.1%

EXAMPLE 2

Example 1 was repeated with samples of the same batches, the only change being use of another brand of a commercially available sunflower oil, which was dried as in example 1.

The biological factor VIII activities were the following percentages of the initial value before the pasteurization:

Batch I 91.0%
Batch II 98.3%
Batch III 92.7%
AHP Batch 89.0%

It is evident from comparison of examples 1 and 2 that the values for a particular batch do not depend on the brand of sunflower oil used, within the accuracy of measurement in the determination of the activity of biological samples.

EXAMPLE 3

5 g of lyophilized fresh plasma (AHP) were pasteurized in 5 portions, as in example 1, with anhydrous corn oil at 60° C. One portion was worked up as in example 1 after 1, 2½, 5, 24 and 48 hours respectively, and factor VIII, factor IX and factor X were assayed.

The biological activities were the following percentages of the initial value before pasteurization:

|  | F VIII | F IX | F X |
| --- | --- | --- | --- |
| 1 hour | 97.0% | 95.0% | 93.4% |
| 2½ hours | 95.8% | 94.1% | 89.0% |
| 5 hours | 93.4% | 92.3% | 87.5% |
| 24 hours | 87.2% | 85.2% | 80.7% |
| 48 hours | 78.8% | 79.6% | 75.5% |

EXAMPLE 4

Example 3 was repeated, the only difference being use of dried sunflower oil in place of corn oil. The measured activities were:

|  | F VIII | F IX | F X |
| --- | --- | --- | --- |
| 1 hour | 99.7% | 96.7% | 93.0% |
| 2½ hours | 90.6% | 92.4% | 88.2% |
| 5 hours | 84.8% | 85.2% | 84.5% |
| 24 hours | 79.4% | 81.4% | 80.6% |
| 48 hours | 77.7% | 80.0% | 78.3% |

EXAMPLE 5

2 g samples of three new batches of freeze-dried factor VIII preparations were pasteurized in 1 g portions as in example 1 using hardened vegetable fat at 60° C. for 2 and 16 hours. The activities were:

|  | 2 hours | 16 hours |
| --- | --- | --- |
| Batch A | 97.7% | 83.2% |
| Batch B | 99.8% | 91.7% |
| Batch C | 98.3% | 88.7% |

EXAMPLE 6

1 g samples of factor VIII powder from three freeze-dried factor VIII batches and freeze-dried fresh plasma (AHP) were pasteurized with dried lard as in example 1. The factor VIII values after the pasteurization were as follows, relative to 100% initial activity.

| F VIII | Batch I | 78.0% |
| --- | --- | --- |
|  | Batch II | 89.5% |
|  | Batch III | 87.3% |
| AHP |  | 90.1% |

EXAMPE 7

2 g of factor VIII or freeze-dried fresh plasma (AHP) were mixed in 1 g portions with 25 g portions of dried lard at 60° C. 0.5 ml of $H_2O$ was added to one of the factor VIII portions and one of the AHP portions at the start of the pasteurization, which lasted 21.5 hours. After the working up, which was carried out as in example 1, the factor VIII values were determined in the factor VIII samples, and the fibrinogen and factor IX values were determined in the AHP samples, as percentages of the initial activity.

These were for the factor VIII samples:

| | % factor VIII activity |
|---|---|
| without addition | 81.1% |
| with 0.5 ml of H$_2$O | 20.0% |

The values in the AHP were

| | Fibrinogen | Factor IX |
|---|---|---|
| without addition | 96.8% | 85.7% |
| with 0.5 ml of H$_2$O | 1.0% | 21.0% |

EXAMPLE 8

25 g portions of dried lard and 180 mg of CaCl$_2$.2H$_2$O were added to 2 g of factor VIII or freeze-dried fresh plasma in 1 g portions at 60° C., and the mixtures were pasteurized at 60° C. for 21.5 hours.

After the working up, which was carried out as in example 1, the factor VIII values were determined in the factor VIII samples, and the fibrinogen and factor IX values were determined in the AHP samples, as percentages of the initial activity.

These were for the factor VIII samples:

| | % factor VIII |
|---|---|
| without addition | 81.1% |
| with CaCl$_2$.2H$_2$O | 95.8% |

The values in the AHP were:

| | Fibrinogen | Factor IX |
|---|---|---|
| without addition | 96.8% | 85.7% |
| with CaCl$_2$.2H$_2$O | 100.0% | 98.4% |

EXAMPLE 9

1 g of lyophilized factor IX/PPSB-powder was mixed with 10 g corn oil. (The oil had been dried with anhydrous CaCl$_2$ powder at 60° C. for 2 hours and had been separated from the CaCl$_2$ by decantation before mixing with the protein powder). The suspension was heated to 98° C. and pasteurized at this temperature for 30 minutes. After the pasteurization was complete the still warm oil was removed by filtration with suction, and the preparation was then washed four times with n-heptane and then dried in vacuo.

The biological activities were the following percentages of the initial value before the pasteurisation:
factor IX: 73,0%
factor X: 84,2%
factor II: 84,4%

Activated factors could not be detected after pasteurization.

EXAMPLE 10

Example 9 was repeated except that the factor IX/PPSB-complex was heated at 60° C. for 50 hours.

The biological activities were the following percentages of the initial value before pasteurization:
factor IX: 79,6%
factor X: 76,9%
factorII: 77,6%

EXAMPLE 11

Corn oil was dried as described in example 9. 1 g of lyophilized intramuscularly (i.m.) injectable gamma-globulin powder was suspended in 10 g dried corn oil. The suspension was pasteurized at 60° C. for 50 hours and worked up as described in example 9. The molecular weight distribution before and after pasteurization was determined in an analytical ultracentrifuge. The measured values were:

| | before pasteurization | after pasteurization (98° C., 30') | after pasteurization (60° C., 50 h) |
|---|---|---|---|
| splitting products (about 5 S) | 0,6% | 0,4% | 0,8% |
| 7 S Gammaglobulin | 87,6% | 88,2% | 86,2% |
| 10 S Dimers | 9,0% | 8,0% | 8,2% |
| >15 S Polymers | 2,8% | 3,4% | 4,8% |

What we claim is:

1. A process for the pasteurization of dried plasma proteins and plasma protein fractions by heat treatment of their suspensions in a liquid organic heat-transfer agent without essentially impairing their biological activity, which comprises carrying out the heat treatment in symmetrical or in mixed glycerol esters, which are liquid at the pasteurization temperature, of saturated or singly or multiply unsaturated fatty acids having 4-22 carbon atoms, or mixtures of these esters, as the inert heat-transfer agent, with the maximum water content of the suspension being 1% by weight and the temperature being 50°-120° C.

2. The process as claimed in claim 1, wherein biological oils or fats of vegetable origin are used as heat-transfer agents.

3. The process as claimed in claim 1, wherein milk or tissue fats of animal origin are used as heat-transfer agents.

4. The process as claimed in claim 1, wherein semi-synthetic fats which have been obtained by fat hardening of the glycerol esters occurring in natural fats and oils are used as heat-transfer agents.

5. The process as claimed in claim 1, wherein the heat treatment is carried out with the water content of the suspension not exceeding 0.5% by weight.

6. The process as claimed in claim 1, wherein the heat treatment is carried out in the presence of Ca salts in the suspension in an amount of 10 to 50 mmol per liter.

7. The process as claimed in claim 1, wherein the heat treatment is carried out at temperatures of 60°-70° C. and with a pasteurization time of 10 to 48 hours.

8. The process as claimed in claim 1, wherein the plasma protein or the plasma protein fractions are, after the pasteurization is complete, removed from the suspension by filtration, washed with an anhydrous volatile organic solvent in which the heat-transfer agent is readily soluble and then dried in a non-damaging way.

* * * * *